United States Patent [19]

Dettbarn et al.

[11] 4,411,650
[45] Oct. 25, 1983

[54] PISTON PUMP FOR NEEDLE-LESS INJECTION INSTRUMENTS

[75] Inventors: Hans-Jürgen Dettbarn, Marburg; Josef Zimmermann, Sulzbach, both of Fed. Rep. of Germany

[73] Assignee: Hoechst Aktiengesellschaft, Frankfurt am Main, Fed. Rep. of Germany

[21] Appl. No.: 368,170

[22] Filed: Apr. 14, 1982

[30] Foreign Application Priority Data

Apr. 16, 1981 [DE] Fed. Rep. of Germany ....... 3115372

[51] Int. Cl.³ ............................................. A61M 5/30
[52] U.S. Cl. ..................................................... 604/72
[58] Field of Search ...................... 604/72, 68, 70, 71, 604/140, 148, 149, 150, 131, 181

[56] References Cited

U.S. PATENT DOCUMENTS

| | | | |
|---|---|---|---|
| 3,057,349 | 10/1962 | Ismach | 604/71 |
| 3,130,723 | 4/1964 | Venditty et al. | 604/70 |
| 3,202,151 | 8/1965 | Kath | 604/71 |
| 3,330,277 | 7/1967 | Gabriels | 604/71 |

*Primary Examiner*—John D. Yasko
*Attorney, Agent, or Firm*—Curtis, Morris & Safford

[57] ABSTRACT

In this piston pump, the pump housing (1) is provided with a mounting (E) for a vessel (3), which consists of a pipe end (4) provided with a hollow needle (5) and of a connecting element (9, 16, 17) for connecting the vessel (3) to the pipe end (4). The pump housing (1) has an inlet channel (7) which is connected to a channel (6) in the pipe end (4).

So that the vessels (3) can be connected rigidly to the piston pump, the connecting element consists, for example, of a metal sheet (9) bent in the form of a U, which is provided on its inner side with U-shaped yokes (10, 11), the yoke (10) facing the pump housing (9) engaging into a groove (12) provided in the pipe end (4) and the other yoke (11) serving for surrounding the vessel neck.

4 Claims, 3 Drawing Figures

PISTON PUMP FOR NEEDLE-LESS INJECTION INSTRUMENTS

The invention relates to a piston pump for needle-less injection instruments, in which the pump housing has a mounting for a vessel for the medium to be injected, this mounting consisting of a pipe end which is provided with a hollow needle for receiving the vessel and which is part of the pump housing and of a connecting element for connecting the vessel to the pipe end, the pump housing having an inlet channel which is connected to a channel in the pipe end.

Piston pumps of the type mentioned are known from German Auslegeschrift No. 1,491,833 and U.S. Pat. No. 3,526,225.

According to German Auslegeschrift No. 1,491,833, fastened to the housing of the vaccine pump is a bearing plate which carries a medicine tube and an air tube as well as the medicine vessel. The medicine vessel is fixed firmly by means of a clamp-on abutment—a kind of clamp—consisting of a stopper, a bracket and telescopically arranged tubes which are fastened to the bearing plate. This construction is complicated to handle. Vessels of different diameters can be used to only a limited extent. Furthermore, this type of mounting for the vessel considerably increases the weight of the piston pump and consequently that of the injection instrument.

According to U.S. Pat. No. 3,526,225, the vessel for the vaccine is held on the needle connection by means of a resilient mounting made of wire. A disadvantage of this type of mounting is that, although the vessel is protected against wobbling by the wire clamps, nevertheless it is not protected against slipping out. The needle connection also has no elements which would prevent the junction between the vessel and the needle connection from sliding apart. Furthermore, here also, vessels of different diameters can be used to only a limited extent.

The invention is intended to remedy this. The invention, as defined in the claims, achieves the object by an arrangement wherein the connecting element consists of a metal sheet bent in the form of a U, which is provided on its inner side with U-shaped yokes, the yoke facing the pump housing engaging into a groove provided in the pipe end and the other yoke serving for surrounding the vessel neck.

In another design, the connecting element consists of a needle connection which is connected to the pipe end and which carries the hollow needle and has a peg with an undercut through which the hollow needle is guided, and a spring element which presses the vessel against the undercut is arranged telescopically round the needle connection. A venting tube can be located in the hollow needle. The needle can project through the needle connection into the pipe end which is provided with an O-ring for sealing off the needle.

The advantages achieved by means of the invention are to be seen essentially in the fact that the vessel for the medium to be injected can be connected rigidly to the piston pump in a simple way. This type of connection is possible for all conventional vessels by means of the mounting according to the invention.

The invention is explained in more detail below with reference to a drawing which illustrates only one form of construction and in which.

Figure 1:
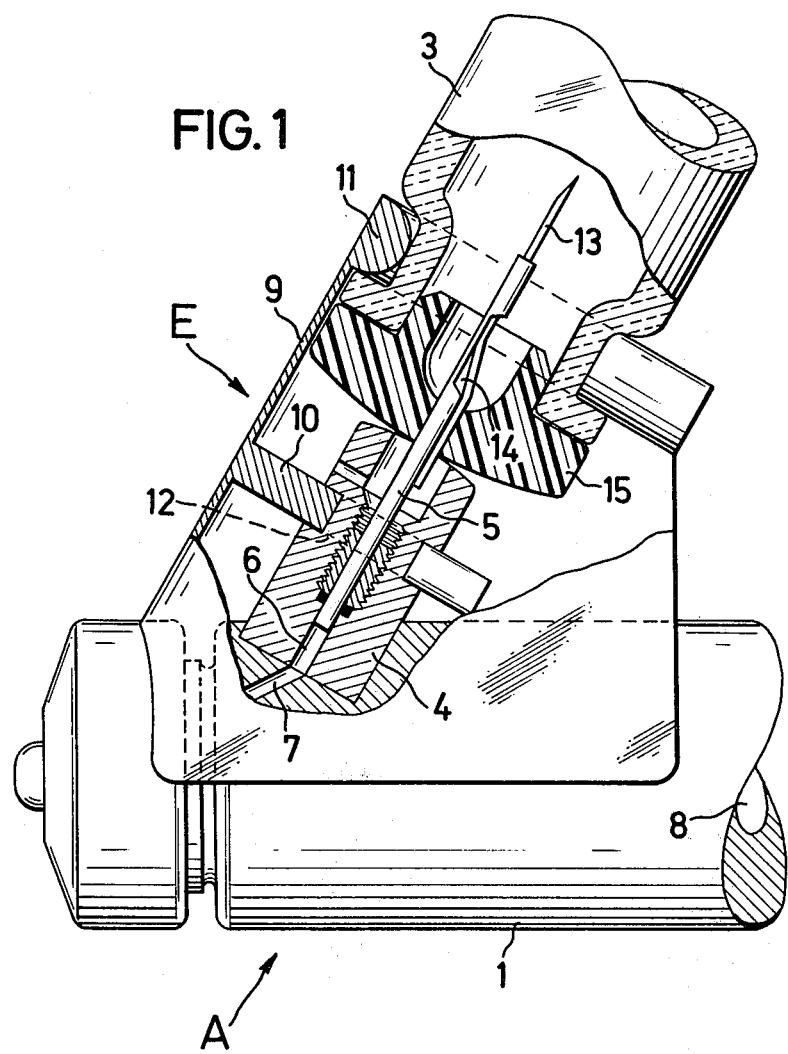
FIG. 1 shows, partially in section, a side view of the piston pump with the vessel attached.

The pump housing (1) of the piston pump A for needle-less injection instruments carries a mounting E for a vessel (3) in which the medium to be injected is located. The mounting E consists of the pipe end (4) and a connecting element which connects the vessel (3) to the pipe end (4). The pipe end (4) which is part of the pump housing can carry a hollow needle (5). The medium to be injected passes via the hollow needle (5), the channel (6) in the pipe end (4) and the inlet channel (7) in the pipe housing (1) from the vessel (3) into the pump chamber (8). The connecting element can consist of a metal sheet (9) bent in the form of a U, which is provided on its inner side with U-shaped yokes (10) and (11). The yoke (10) engages into the groove (12) of the pipe end (4) and the yoke (11) surrounds the vessel neck. The distance between the yokes (10) and (11) is calculated so that, after the vessel (3) has been attached to the hollow needle (5), the pipe end (4) and the vessel (3) are braced against one another via the sheet (9) as a result of the clamping force of the closing stopper (15) of the vessel (3). By attaching a suitable adapter (not shown) onto the upper yoke (11), the metal sheet (9) can be adapted to vessels with different neck sizes.

Located in the hollow needle (5) is a venting tube (13). This is introduced into the hollow needle (5) through a lateral orifice (14). The medium to be injected passes into the hollow needle through the lateral orifice (14) of the hollow needle (5).

Figure 2:
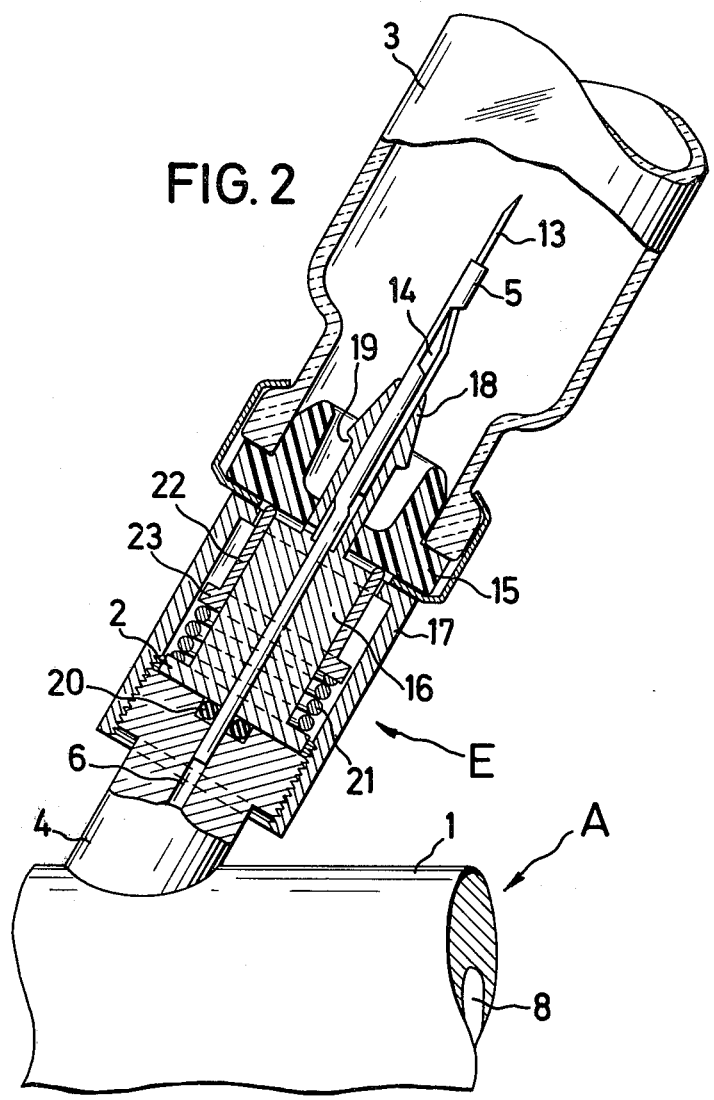
FIG. 2 shows an alternative form of the piston pump according to FIG. 1, with the vessel attached and the spring element tensioned.
Figure 3:
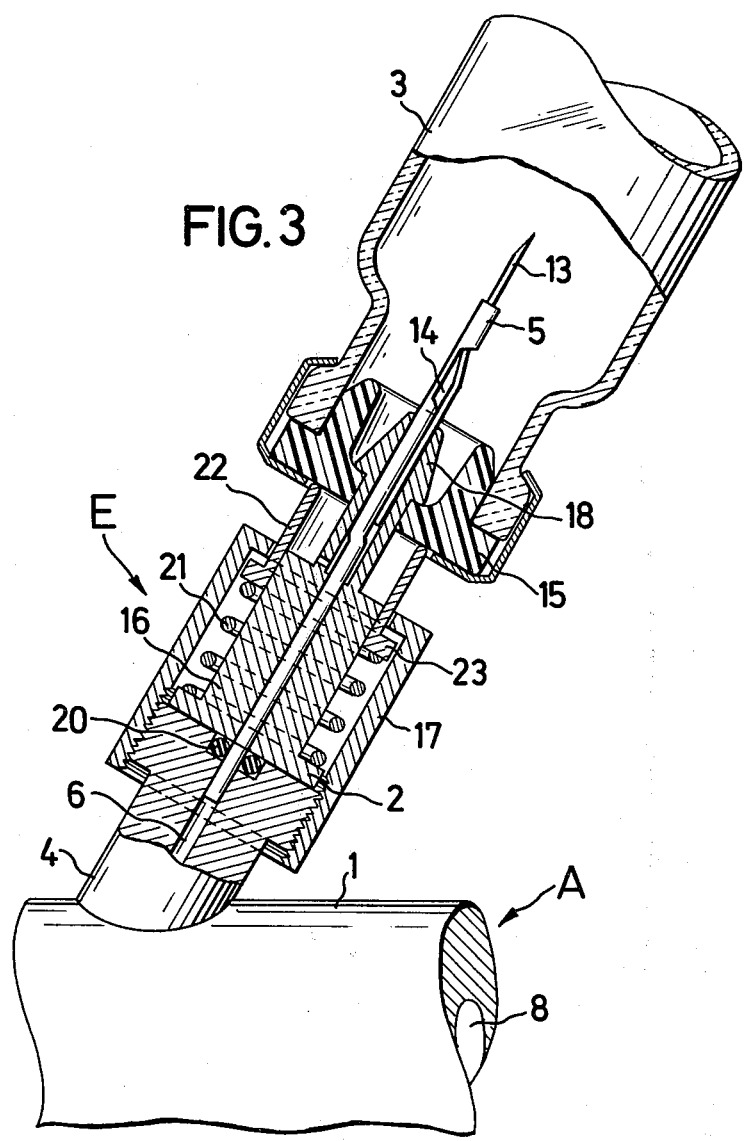
FIG. 3 shows the attached vessel pressed against the undercut.

In an alternative form (FIGS. 2 and 3), the connecting element consists of a needle connection (16) which is connected to the pipe end (4), for example by means of a box nut (17). The needle connection (16) has a peg (18) with undercuts (19) through which the hollow needle (5) is guided. It may be expedient for the hollow needle (5) to project into the pipe end (4). It is then sealed off there by means of an O-ring (20). A spring element is arranged telescopically round the needle connection. It consists of a compression spring (21) and of a sleeve (22) with a bead (23). The compression spring (21) is supported at one end on the bead (23) and at the other end on the flange (2) of the needle connection (16). When the vessel (3) is attached to the needle connection (16), the venting tube (13), the hollow needle (5) and the peg (18) pass through the closing stopper (15) of the vessel (3). The vessel (3) is pushed over the peg (18) until the closing stopper (15) engages behind the undercut (19) of the peg (18). During this time, the compression spring (21) is compressed by the sleeve (22). When the vessel (3) is released, the compression spring (21) pushes the vessel (3) back via the sleeve (22) until the closing stopper (15) rests against the undercut (19) of the peg (18).

We claim:

1. A piston pump for needle-less injection instruments, in which the pump housing has a mounting for a vessel for the medium to be injected, this mounting consisting of a pipe end which is provided with a hollow needle for receiving the vessel and which is part of the pump housing and of a connecting element for connecting the vessel to the pipe end, the pump housing having an inlet channel connected to a channel in the pipe end, wherein the connecting element consists of a metal sheet (9) bent in the form of a U, which is provided on its inner side with U-shaped yokes (10, 11), the yoke (10) facing the pump housing (1) engaging into a groove (12) provided in the pipe end (4) and the other yoke (11) serving for surrounding the vessel neck.

2. A piston pump for needle-less injection instruments, in which the pump housing has a mounting for a vessel for the medium to be injected, which consists of a pipe end which is provided with a hollow needle for receiving the vessel and which is part of the pump housing and of a connecting element for connecting the vessel to the pipe end, the pump housing having an inlet channel connected to a channel in the pipe end, wherein the connecting element consists of a needle connection (16) which is connected to the pipe end (4) and carries the hollow needle (5) and which has a peg (18) with an undercut (19), through which the hollow needle (5) is guided, there being arranged telescopically round the needle connection (16) a spring element which presses the vessel against the undercut (19).

3. The piston pump as claimed in claim 1 or 2, wherein a venting tube (13) is located in the hollow needle (5).

4. The piston pump as claimed in claim 2, wherein the hollow needle (5) projects through the needle connection (16) into the pipe end (4) which is provided with an O-ring (20) for sealing off the hollow needle.

* * * * *